(12) United States Patent
Adams

(10) Patent No.: US 9,819,843 B2
(45) Date of Patent: Nov. 14, 2017

(54) HEAD-MOUNTED SYSTEMS AND METHODS FOR PROVIDING INSPECTION, EVALUATION OR ASSESSMENT OF AN EVENT OR LOCATION

(71) Applicant: Zeriscope Inc., Charleston, SC (US)

(72) Inventor: Robert J. Adams, Mount Pleasant, SC (US)

(73) Assignee: Zeriscope Inc., Charleston, SC (US)

( * ) Notice: Subject to any disclaimer, the term of this patent is extended or adjusted under 35 U.S.C. 154(b) by 0 days.

(21) Appl. No.: 14/430,005

(22) PCT Filed: Sep. 20, 2013

(86) PCT No.: PCT/US2013/060848
§ 371 (c)(1),
(2) Date: Mar. 20, 2015

(87) PCT Pub. No.: WO2014/047402
PCT Pub. Date: Mar. 27, 2014

(65) Prior Publication Data
US 2015/0244903 A1 Aug. 27, 2015

Related U.S. Application Data

(60) Provisional application No. 61/703,434, filed on Sep. 20, 2012.

(51) Int. Cl.
*H04N 5/222* (2006.01)
*G09G 5/00* (2006.01)
(Continued)

(52) U.S. Cl.
CPC ......... *H04N 5/2252* (2013.01); *G02B 27/017* (2013.01); *G02B 27/0172* (2013.01);
(Continued)

(58) Field of Classification Search
CPC .......... G02B 27/017; G02B 2027/0178; G02B 2027/0118; G02B 27/0093;
(Continued)

(56) References Cited

U.S. PATENT DOCUMENTS 8,872,766 B2 * 10/2014 Moore ................... G02B 27/01
345/157
2002/0118284 A1 8/2002 Newman et al.
(Continued)

FOREIGN PATENT DOCUMENTS

| JP | 2008085548 | 4/2008 |
| WO | 2011044680 | 4/2011 |

OTHER PUBLICATIONS

EyeQ2, Vision System on a Chip, Sep. 2007 (4 pages).
(Continued)

*Primary Examiner* — Trung Diep
(74) *Attorney, Agent, or Firm* — Finch Paolino, LLC

(57) ABSTRACT

Systems and methods for providing assessment of a local scene to a remote location are provided herein. The systems and methods facilitate collection, storage and transmission of data from the local scene to the remote location without limiting the mobility, dexterity, adaptability and interactive capability of an on-scene technician. For example, a head-mounted device according to an implementation discussed herein can include: a head-mounted frame that is configured to hold a transparent visor; an image capturing device attachable to at least one of the head-mounted frame and the transparent visor; and a micro-optic display system attachable to at least one of the head-mounted frame and the transparent visor. The micro-optic display system can be configured to render a heads up image on the transparent visor. In addition, the heads up image can define an outline of a field of view of the image capturing device.

20 Claims, 8 Drawing Sheets

(51) Int. Cl.
| | |
|---|---|
| H04N 5/225 | (2006.01) |
| G02B 27/01 | (2006.01) |
| H04N 5/232 | (2006.01) |
| G06F 3/01 | (2006.01) |
| G06F 3/0338 | (2013.01) |
| G06T 11/00 | (2006.01) |
| G06F 3/0362 | (2013.01) |
| G06T 7/00 | (2017.01) |
| A61B 5/00 | (2006.01) |
| G06F 19/00 | (2011.01) |

(52) U.S. Cl.
CPC ............ *G06F 3/012* (2013.01); *G06F 3/0338* (2013.01); *G06F 3/0362* (2013.01); *G06T 7/0012* (2013.01); *G06T 11/00* (2013.01); *H04N 5/23293* (2013.01); *H04N 5/23296* (2013.01); *A61B 5/0002* (2013.01); *G02B 2027/014* (2013.01); *G02B 2027/0123* (2013.01); *G02B 2027/0127* (2013.01); *G02B 2027/0138* (2013.01); *G02B 2027/0178* (2013.01); *G06F 19/3406* (2013.01)

(58) Field of Classification Search
CPC ........ G02B 27/0172; G02B 2027/0127; G02B 2027/0123; G02B 2027/0138; G02B 23/125; G06F 1/163; G06F 3/013; G06F 3/011; G06F 3/005
See application file for complete search history.

(56) References Cited

U.S. PATENT DOCUMENTS

| | | | |
|---|---|---|---|
| 2002/0163486 A1* | 11/2002 | Ronzani | G02B 27/017 345/87 |
| 2005/0206583 A1 | 9/2005 | Lemelson et al. | |
| 2006/0152618 A1 | 7/2006 | Yamasaki | |
| 2008/0122736 A1* | 5/2008 | Ronzani | G02B 27/017 345/8 |
| 2008/0170130 A1 | 7/2008 | Ollila et al. | |
| 2009/0153468 A1* | 6/2009 | Ong | G06F 3/011 345/156 |
| 2010/0141554 A1 | 6/2010 | Devereaux et al. | |
| 2011/0043644 A1 | 2/2011 | Munger et al. | |
| 2011/0231757 A1 | 9/2011 | Haddick et al. | |
| 2011/0238079 A1 | 9/2011 | Hannaford et al. | |
| 2012/0019645 A1 | 1/2012 | Maltz | |
| 2012/0218301 A1* | 8/2012 | Miller | G02B 27/017 345/633 |

OTHER PUBLICATIONS

"Contour Launching First Camera and Goggle Connectivity App at SIA," Jan. 26, 2012, available at morocross.transworld.net (last accessed Mar. 19, 2015) (3 pages).

"Game Maker Without a Rule Book," Sep. 8, 2012, available at NYTimes.com (last accessed Mar. 19, 2015) (7 pages).

Augmented Reality Products, WRAP 920AR, available at vuxix.com (last accessed Sep. 12, 2012) (2 pages).

International Search Report and Written Opinion for corresponding PCT App. No. PCT/US2013/060848, dated Dec. 17, 2013 (16 pages).

* cited by examiner

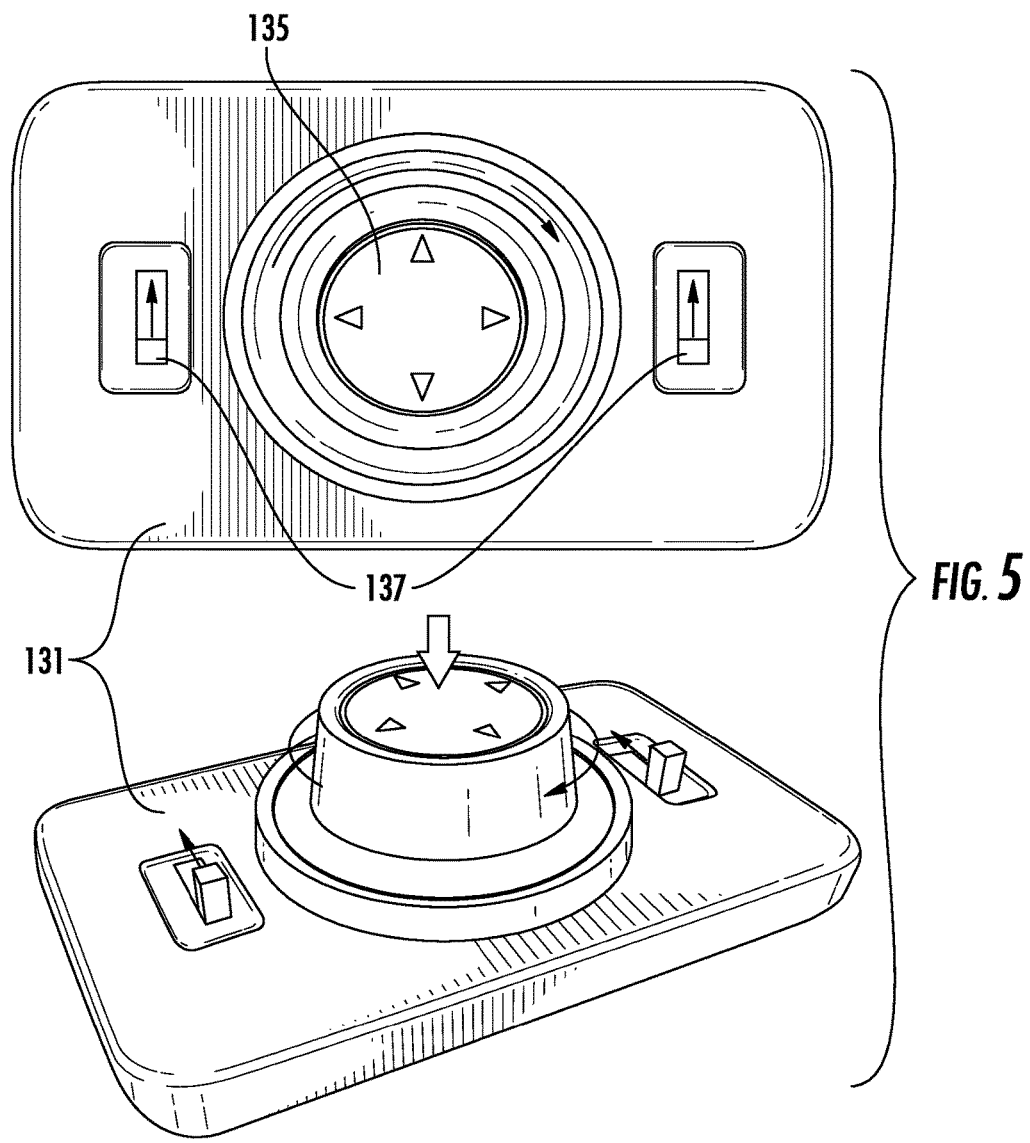

HEAD-MOUNTED SYSTEMS AND METHODS FOR PROVIDING INSPECTION, EVALUATION OR ASSESSMENT OF AN EVENT OR LOCATION

CROSS-REFERENCE TO RELATED APPLICATIONS

This application claims the benefit of U.S. Provisional Patent Application Ser. No. 61/703,434, filed on Sep. 20, 2012, entitled "SYSTEMS AND METHODS FOR PROVIDING ASSESSMENT OF A SCENE TO A REMOTE LOCATION," the disclosure of which is expressly incorporated herein by reference in its entirety.

BACKGROUND

The human brain is capable of outperforming a computer in recognizing patterns based on learning and experience. The ability to have the most "experienced eyes" (really the "experienced brain"), regardless of where that person or those persons are located, participate in the testing, inspection or certification of manufacturing installations, equipment, constructions sites, power plants or other complex industrial or in the evaluation and management of crisis situations such as mass casualty, terrorist attacks, crime scenes, medical crises, radiation emergencies, bomb threats, etc. and providing the best possible solutions is a major advantage when compared to having only less experienced resources on site. The situation commonly arises where the problem (or situation, scene, etc.) is in one location and the expertise to address the problem is located elsewhere and perhaps in several disparate locations worldwide. For example, few persons have had the challenge of disarming a bomb, and in such situations, it is hard to imagine that the person at risk would not want to have the world's experts in bomb disarmarmament looking over his shoulder as he cut one wire and not another. Additionally, in the construction and maintenance of highly complex facilities such as power plants, oil drilling rigs, sophisticated manufacturing facilities, etc., for example, there can be a need for visual inspection either during the normal construction and operation of the facility—to insure all domains are within "spec", or at times where repair or remedy is required.

Another example is in the field of telemedicine whereby information technologies are used to provide clinical care at a distance. Telemedicine involves collecting and transmitting medical information from a local scene to a remote expert. By providing the remote expert with medical information, the remote expert can provide clinical care without being present at the local scene. Thus, telemedicine facilitates the provision of expert medical care to remote locations, which may not be accessible to the expert. However, telemedicine is typically provided using fixed telemedicine platforms such as rolling carts or fixed workstations. Telemedicine platforms, therefore, can limit the mobility, adaptability and interactive capability of an on-scene technician, and are not adapted for many real world situations in which technical evaluation and interaction—whether in medical, public safety, or industrial environments and/or any other situation—is needed

SUMMARY

Systems and methods for providing inspection, evaluation, assessment and/or certification of a location, structure, event, etc. are provided herein. Optionally, the systems and methods can provide assessment of a local scene (e.g., a facility, construction site, crisis, medical site or any other event, location or structure) to a remote location. The systems and methods facilitate collection, storage and transmission of data (e.g., audio, video, and any other data) from the local scene to the remote location without limiting the mobility, dexterity, adaptability and interactive capability of an on-scene technician. The systems and methods can facilitate the exchange of information between the on-scene technician and the remote location, which can be staffed by one or more experts. Whether performing certification inspections, evaluating construction according to specifications, performing third party inspections (TPI) or second party inspections (SPI), providing first party intelligence during critical phases of construction, development or operation of complex machines, operations, facilities or sites, or working crime scenes, highway accidents, mass casualty or risk situations of any kind, the contribution of experienced experts in the field can be key to situation resolution.

For example, a head-mounted device according to an implementation discussed herein can include: a head-mounted frame that is configured to hold a transparent visor; an image capturing device attachable to at least one of the head-mounted frame and the transparent visor; and a micro-optic display system attachable to at least one of the head-mounted frame and the transparent visor. The micro-optic display system can be configured to render a heads up image on the transparent visor. In addition, the heads up image can define an outline of a field of view of the image capturing device.

Optionally, the outline of the field of view frames a scene captured by the image capturing device. For example, dimensions of the outline of the field of view are related to an amount of zoom of the image capturing device.

In some implementations, the micro-optic display system includes: an image generator configured to project the heads up image on the transparent visor; a processor; and a memory communicatively connected to the processor. The memory can have computer-executable instructions stored thereon that, when executed by the processor, cause the processor to: receive operating characteristics of the image capturing device; determine a field of view based on the operating characteristics; and determine dimensions of the outline of the field of view. For example, the operating characteristics of the image capturing device can include at least one of an effective focal length and an amount of digital zoom.

Additionally, the transparent visor can be movable between an active position and an inactive position in some implementations. For example, the image capturing device can be in an operating state when the transparent visor is in the active position. Optionally, the transparent visor can shield at least a portion of a user's face when the transparent visor is in the active position.

In some implementations, the heads up image includes at least one graphical information field. In addition, the heads up image can include a first region defined by the outline of the field of view and a second region including the graphical information field. Optionally, the outline of the field of view can be provided in the gaze forward position. Optionally, the graphical information field can be provided in the peripheral viewing area such as above, below, left or right of the gaze forward position. Optionally, the second region can be located adjacent to the outline of the field of view. In some implementations, the second region does not overlap with the first region.

The graphical information field can optionally include medical information in some implementations. For example, the medical information can include vital sign data for at least one patient such as at least one of temperature, blood pressure, heart rate, oxygen saturation and EKG data. Alternatively or additionally, the graphical information field can include technical or situational information such as schematics, floor plans, wiring diagrams, regulations, specifications, images, etc. Alternatively or additionally, the graphical information field can include a status of the image capturing device. Alternatively or additionally, the graphical information field can include extrinsic information (e.g., any information provided by an external source).

In some implementations, the image capturing device can be a video capturing device. Alternatively or additionally, the image capturing device can be a light field camera.

The head-mounted device can also include a microphone attachable to at least one of the head-mounted frame and the transparent visor. Alternatively or additionally, the head-mounted device can also include a speaker attachable to at least one of the head-mounted frame and the transparent visor. In some implementations, the speaker is configured to project an audio signal only to a user of the head-mounted device. In other implementations, the speaker is configured to project an audio signal to a user of the head-mounted device and one or more persons at a local scene.

Optionally, the head-mounted device can include a bar code reader system attachable to at least one of the head-mounted frame and the transparent visor in some implementations. Alternatively or additionally, the head-mounted device can also include an interface configured to receive medical information. For example, the interface can be a wireless receiver configured to receive vital sign data for at least one patient from one or more medical instruments over a wireless communication link. The wireless receiver can optionally be a Bluetooth receiver, for example. Optionally, the head-mounted device can include one or more sensors such as an infrared sensor or a radiation sensor, for example.

In some implementations, the head-mounted device can include a protective headgear that encases at least a portion of the head-mounted frame. Optionally, the headgear can be custom-fitted to the user of the head-mounted device.

Alternatively or additionally, the micro-optic display system can optionally be further configured to render or display a zoom box in addition to the outline of the field of view as part of the heads up image displayed on the transparent visor. Optionally, the zoom box can be used to display a magnified view of the portion of the local scene contained within the outline of the field of view (e.g., the image displayed at the remote station) to the user of the head-mounted device via the heads up image. Optionally, the zoom box can be displayed away from the user's line of sight to minimize distraction. Optionally, the zoom box can be displayed at a peripheral portion of the heads up image such as above, below, left or right of the outline of the field of view.

In another implementation, a mobile assessment system can include: a head-mounted device and a command unit. The head-mounted device can include: a head-mounted frame that is configured to hold a transparent visor; a video capturing device attachable to at least one of the head-mounted frame and the transparent visor; a micro-optic display system attachable to at least one of the head-mounted frame and the transparent visor; and a command unit interface. The micro-optic display system can be configured to render a heads up image on the transparent visor. In addition, the heads up image can define an outline of a field of view of the video capturing device. The command unit can include: a head-mounted device interface communicatively connected to the command unit interface of the head-mounted device through a first communication link; a command unit processor; and a command unit memory communicatively connected to the command unit processor. The command unit memory can have computer-executable instructions stored thereon that, when executed by the command unit processor, cause the command unit processor to: receive data from the head-mounted device interface over the first communication link; and transmit the data over a second communication link to a remote station.

Optionally, the outline of the field of view frames a scene captured by the video capturing device. For example, dimensions of the outline of the field of view are related to an amount of zoom of the video capturing device.

In some implementations, the micro-optic display system includes: an image generator configured to project the heads up image on the transparent visor; a processor; and a memory communicatively connected to the processor. The memory can have computer-executable instructions stored thereon that, when executed by the processor, cause the processor to: receive operating characteristics of the video capturing device; determine a field of view based on the operating characteristics; and determine dimensions of the outline of the field of view. For example, the operating characteristics of the video capturing device can include at least one of an effective focal length and an amount of digital zoom.

Additionally, the transparent visor can be movable between an active position and an inactive position in some implementations. For example, the video capturing device can be in an operating state when the transparent visor is in the active position. Optionally, the transparent visor can shield at least a portion of a user's face when the transparent visor is in the active position.

In some implementations, the heads up image can include at least one graphical information field. In addition, the heads up image can include a first region defined by the outline of the field of view and a second region including the graphical information field. Optionally, the second region can be located adjacent to the outline of the field of view. In some implementations, the second region does not overlap with the first region.

The graphical information field can optionally include medical information in some implementations. For example, the medical information can include vital sign data for at least one patient such as at least one of temperature, blood pressure, heart rate, oxygen saturation and EKG data. Alternatively or additionally, the graphical information field can include a status of the video capturing device. Alternatively or additionally, the graphical information field can include extrinsic information (e.g., any information provided by an external source).

The head-mounted device can also include a microphone attachable to at least one of the head-mounted frame and the transparent visor. Alternatively or additionally, the head-mounted device can also include a speaker attachable to at least one of the head-mounted frame and the transparent visor. In some implementations, the speaker is configured to project an audio signal only to a user of the head-mounted device. In other implementations, the speaker is configured to project an audio signal to a user of the head-mounted device and one or more persons at a local scene.

Optionally, the head-mounted device can include a bar code reader system attachable to at least one of the head-mounted frame and the transparent visor in some implementations. Alternatively or additionally, the head-mounted device can also include an interface configured to receive medical information. For example, the interface can be a wireless receiver configured to receive vital sign data for at least one patient from one or more medical instruments over a wireless communication link. The wireless receiver can optionally be a Bluetooth receiver. Optionally, the head-mounted device can include one or more sensors such as an infrared sensor or a radiation sensor, for example, to provide information to both the user and the remote location.

In some implementations, the first communication link can be a wireless communication link. Alternatively or additionally, the second communication link can be at least one of a mobile telecommunication link, a satellite link, a radiofrequency channel or a computer network link. Optionally, the data is at least one of video data and audio data.

In some implementations, the command unit memory can have further computer-executable instructions stored thereon that, when executed by the command unit processor, cause the command unit processor to establish a secure connection with the remote station prior to transmitting the data over the second communication link. Alternatively or additionally, the command unit memory can have further computer-executable instructions stored thereon that, when executed by the command unit processor, cause the command unit processor to encrypt the data prior to transmitting the data over the second communication link.

Optionally, the data can be received at the head-mounted device interface over the first communication link and transmitted from the command unit over the second communication link to the remote station in near real-time. Alternatively, the command unit memory can have further computer-executable instructions stored thereon that, when executed by the command unit processor, cause the command unit processor to: receive the data at the head-mounted device interface over the first communication link at a first time; store the data in the command unit memory; establish a connection with the remote station over the second communication link; and transmit the data over the second communication link to the remote station at a second time.

In some implementations, the command unit further comprises a video capturing device control unit. The video capturing device control unit can be configured to control an amount of zoom of the video capturing device by transmitting control signals to the video capturing device over the first communication link. The video capturing device control unit can be configured to control optical zoom functions and/or digital zoom functions of the video capturing device. For example, the video capturing device control unit can be a rotary dial. Alternatively or additionally, the video capturing device control unit can be further configured to receive voice commands from a user of the mobile assessment system and correlate the voice commands with the control signals. Alternatively or additionally, the video capturing device control unit can be further configured to implement eye tracking technology, blink switching, etc. to generate control signals. This disclosure contemplates that voice activation and/or eye tracking, blink switching, etc. can optionally replace or optionally augment manual control of the video capturing device. Alternatively or additionally, the video capturing device control unit can be further configured to receive the control signals from the remote station. For example, the video capturing device control unit can be further configured to receive voice command from the remote station and correlate the voice commands with the control signals.

In some implementations, the data received at the head-mounted device interface includes audio data, and the command unit memory has further computer-executable instructions stored thereon that, when executed by the command unit processor, cause the command unit processor to: perform a voice recognition algorithm on the audio data; identify at least one person using the voice recognition algorithm; and transmit to the head-mounted device over the first communication link information relating to an identity of the at least one person. Optionally, the heads up image can include at least one graphical information field including the information relating to the identity of the at least one person.

Alternatively or additionally, the data received at the head-mounted device interface includes audio data, and the command unit memory has further computer-executable instructions stored thereon that, when executed by the command unit processor, cause the command unit processor to: transmit the audio data to the remote station over the second communication link; and receive information relating to an identity of the at least one person from the remote station over the second communication link. The information relating to the identity of the at least one person can be obtained by performing a voice recognition algorithm at the remote station. Optionally, the heads up image can include at least one graphical information field including the information relating to the identity of the at least one person.

In some implementations, the data received at the head-mounted device interface includes video data, and the command unit memory has further computer-executable instructions stored thereon that, when executed by the command unit processor, cause the command unit processor to: perform a facial recognition algorithm on the video data; identify at least one person using the facial recognition algorithm; and transmit to the head-mounted device over the first communication link information relating to an identity of the at least one person. Optionally, the heads up image can include at least one graphical information field including the information relating to the identity of the at least one person.

Alternatively or additionally, the data received at the head-mounted device interface includes video data, and the command unit memory has further computer-executable instructions stored thereon that, when executed by the command unit processor, cause the command unit processor to: transmit the video data to the remote station over the second communication link; and receive information relating to an identity of the at least one person from the remote station over the second communication link. The information relating to the identity of the at least one person can be obtained by performing a facial recognition algorithm at the remote station. Optionally, the heads up image can include at least one graphical information field including the information relating to the identity of the at least one person.

In some implementations, the command unit memory can have further computer-executable instructions stored thereon that, when executed by the command unit processor, cause the command unit processor to: receive an audio signal from the remote station over the second communication link; and transmit the audio signal to the head-mounted device over the first communication link. Optionally, the head-mounted device can further include a speaker attachable to at least one of the head-mounted frame and the transparent visor, and the head-mounted device can be further configured to: receive the audio signal at the command unit interface over the first communication link; and project the audio signal using the speaker. In some implementations, the speaker can be configured to project the audio signal only to a user of the mobile assessment system.

Alternatively or additionally, the speaker can be configured to project the audio signal to a user of the mobile assessment system and one or more persons at a local scene.

In some implementations, the command unit memory has further computer-executable instructions stored thereon that, when executed by the command unit processor, cause the command unit processor to: receive extrinsic information data from the remote station over the second communication link; and transmit the extrinsic information data to the head-mounted device over the first communication link. The heads up image can include at least one graphical information field including the extrinsic information data.

In some implementations, the command unit is attachable to at least one of the head-mounted frame and the transparent visor.

Alternatively or additionally, the micro-optic display system can optionally be further configured to render or display a zoom box in addition to the outline of the field of view as part of the heads up image displayed on the transparent visor. Optionally, the zoom box can be used to display a magnified view of the portion of the local scene contained within the outline of the field of view (e.g., the image displayed at the remote station) to the user of the head-mounted device. Optionally, the zoom box can be displayed away from the user's line of sight to minimize distraction. Optionally, the zoom box can be displayed at a peripheral portion of the heads up image such as above, below, left or right of the outline of the field of view.

In yet another implementation, a method for assessing a local scene using a mobile assessment system as discussed above includes: capturing a video image with the video capturing device; transmitting the video image to a remote station over a communication link; and projecting the heads up image on the transparent visor. The heads up image can include an outline of the field of view of the video capturing device.

Optionally, the method can also include: determining a field of view based on operating characteristics of the video capturing device; and determining dimensions of the outline of the field of view. For example, the operating characteristics of the video capturing device can include at least one of an effective focal length and an amount of digital zoom.

In some implementations, the heads up image can include at least one graphical information field. In addition, the heads up image can include a first region defined by the outline of the field of view and a second region including the graphical information field. Optionally, the second region can be located adjacent to the outline of the field of view. In some implementations, the second region does not overlap with the first region.

The graphical information field can optionally include medical information in some implementations. For example, the medical information can include vital sign data for at least one patient such as at least one of temperature, blood pressure, heart rate, oxygen saturation and EKG data. Alternatively or additionally, the graphical information field can include a status of the image capturing device. Alternatively or additionally, the graphical information field can include extrinsic information (e.g., any information provided by an external source).

In some implementations, the communication link is at least one of a mobile telecommunication link, a satellite link, a radiofrequency channel or a computer network link.

Optionally, the video data is captured by the video capturing device and transmitted over the communication link to the remote station in near real-time. Alternatively or additionally, the method can include: capturing the video data at a first time; storing the video data; establishing a connection with the remote station over the communication link; and transmitting the data over the communication link to the remote station at a second time.

Optionally, the method can also include establishing a secure connection with the remote station prior to transmitting the data over the communication link. Alternatively or additionally, the method can include encrypting the data prior to transmitting the data over the communication link.

In some implementations, the method can include controlling an amount of zoom of the video capturing device. The method can include controlling optical zoom functions and/or digital zoom functions of the video capturing device. For example, the method can optionally include: receiving voice commands from at least one of a user of the mobile assessment system and the remote station; and correlating the voice commands with control signals. The amount of zoom of the video capturing device can be controlled using the control signals.

In some implementations, the method can further include: performing at least one of a voice recognition algorithm or a facial recognition algorithm on the video data; and identifying information relating to at least one person using the voice recognition algorithm or the facial recognition algorithm. Optionally, the heads up image can include at least one graphical information field including the information relating to the identity of the at least one person.

In some implementations, the method can include: transmitting the video data to the remote station over the communication link; and receiving information relating to an identity of the at least one person from the remote station over the communication link. The information relating to the identity of the at least one person can be obtained by performing at least one of a voice recognition algorithm or a facial recognition algorithm at the remote station. Optionally, the heads up image can include at least one graphical information field including the information relating to the identity of the at least one person.

In some implementations, the head-mounted device includes a speaker attachable to at least one of the head-mounted frame and the transparent visor. The method can optionally include: receiving an audio signal from the remote station over the communication link; and projecting the audio signal using the speaker.

In some implementations, the method can include receiving extrinsic information data from the remote station over the communication link. The heads up image can optionally include at least one graphical information field including the extrinsic information data.

Alternatively or additionally, the method can optionally further include projecting or displaying a zoom box in addition to the outline of the field of view as part of the heads up image displayed on the transparent visor. Optionally, the zoom box can be used to display a magnified view of the portion of the local scene contained within the outline of the field of view (e.g., the image displayed at the remote station) to the user of the head-mounted device. Optionally, the zoom box can be displayed away from the user's line of sight to minimize distraction. Optionally, the zoom box can be displayed at a peripheral portion of the heads up image such as above, below, left or right of the outline of the field of view.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 5 illustrates perspective views of a video capturing device control unit included in the mobile assessment system of FIGS. 1A-1F;

DETAILED DESCRIPTION

Figures 1A, 1B, 1C:
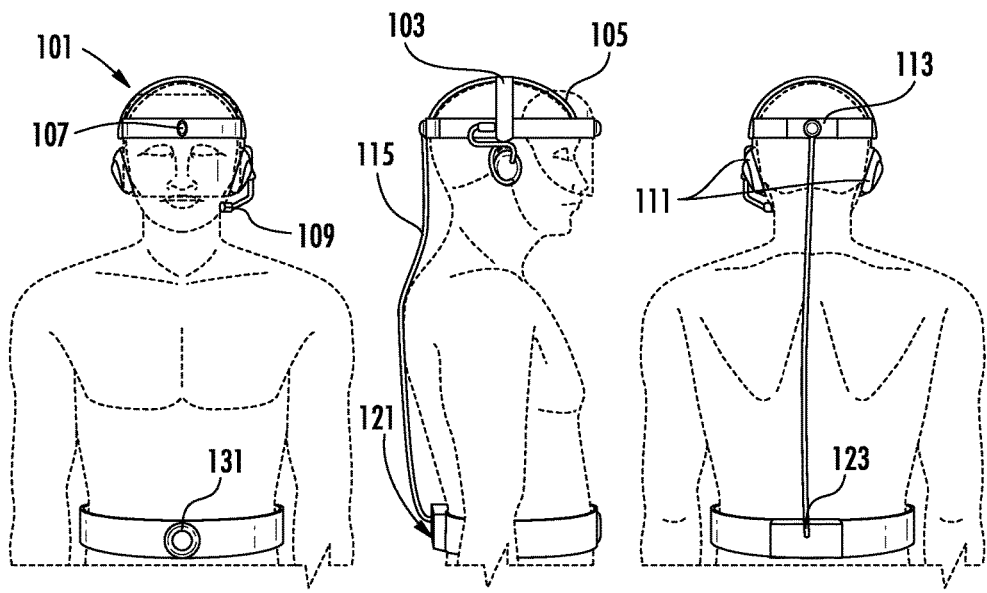
FIGS. 1A-1F are perspective views illustrating a mobile assessment system worn by a user according to implementations discussed herein.
Figures 1D, 1E, 1F:
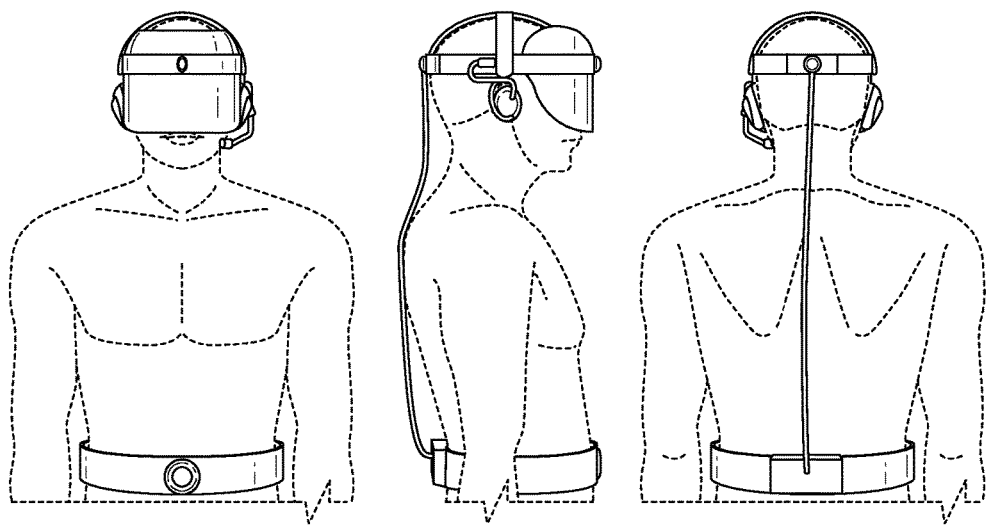

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a", "an", "the", include plural referents unless the context clearly dictates otherwise. The term "comprising" and variations thereof as used herein is used synonymously with the term "including" and variations thereof and are open, non-limiting terms. While implementations will be described for providing assessment of a local scene to a remote location in medical applications, it will become evident to those skilled in the art that the implementations are not limited thereto, but are applicable for providing assessment of a local scene to a remote location in any application. Specifically, this disclosure contemplates a telepresence device for use in any situation. For example, using the systems and methods disclosed herein, it is possible to consult with remote experts/consultants or remotely supervise procedures (e.g., medical and non-medical experts or procedures), provide information from on-scene first responders, provide hazardous situation analysis, triage and stabilization (e.g., in response to mass casualties, terrorist attacks, radiation or HAZMAT casualties, military/battlefield scenarios), provide medical consultations in remote locations (e.g., prisons, deployed ships, aircraft, nursing homes, intensive care units, rural areas, etc.), provide remote forensic pathology, provide remote support to law enforcement personnel (e.g., crowd control, identification of suspicious persons, bomb squads, etc.) and provide remote support for inspections (e.g., NTSB inspections of crash sites, FAA inspections of aircraft engines, etc., including ability to record the inspections and/or training events for subsequent evaluation). In the medical environment, the systems and methods disclosed herein can be used to capture and transmit data (e.g., visual and audio feeds, for example) elicited by examination protocols by an on-scene technician at the local scene to a remote expert. For example, examination protocols can include, but are not limited to, stroke scoring, assessing treatment response, diagnosing concussions (e.g., at sporting events), triaging mass casualties, coding cardiac arrest levels, making psychiatric decisions (e.g., physical restraint, involuntary hospitalization, etc.), escalating care (e.g., transfer from emergency room to intensive care) and staffing intern consultations. It should be understood that this disclosure contemplates systems and methods for providing assessment of a local scene to a remote location in any application, and it should not be limited to the example applications set forth above.

The systems and methods for providing assessment of a local scene to a remote station disclosed herein provide on-site data collection (e.g., audio, video, or any other data), storage and transmission capabilities. For example, the user of the mobile assessment system visits the local scene, which provides the mobility, dexterity, adaptability and interactive capability of having a human being at the local scene. The mobile assessment system facilitates collecting, storing and transmitting data from the local scene to the remote station. Additionally, because the collected data is transmitted to the remote station, a remote expert/consultant can provide advantages of pattern recognition and rapid situation analysis without actually visiting the local scene, which is not practical in many applications. The mobile assessment system provides the remote station with data such that the remote expert/consultant can essentially observe and interact with the local scene without actually being there. The mobile assessment system also provides the capability to feed audio, video and data from the remote station to the local scene. For example, extrinsic information can be fed from the remote station to the local scene. The extrinsic information can include any information that is relevant to the user of the mobile assessment system at the local scene from a remote source (e.g., the remote station) including, but not limited to, information about a patient or other person at the local scene and information the local scene itself. This information can include, but is not limited to, medical data, local scene situation analysis (e.g., contamination risk, radiation levels, satellite images of the local scene, etc.), diagrams or schematics or blueprints (e.g., for facilities inspection, equipment repair, bomb defusing, etc.), and results of advanced back field or cloud-based analyses (e.g., results of facial or voice recognition algorithms). The mobile assessment system can be configured to display the extrinsic information to the user of the mobile assessment system.

Referring now to FIGS. 1A-1F and 2A-2D, perspective views illustrating a mobile assessment system as worn on a user and a head-mounted device included in the mobile assessment system are shown. The mobile assessment system can include a head-mounted device 101 and a command unit 121. Optionally, the head-mounted device 101 and the command unit 121 are configured to facilitate the user having both hands free during an assessment of a local scene. For example, the mobile assessment system can be configured to facilitate the user having both hands free during a telemedicine assessment, such as when a technician performs the assessment and sends information (e.g., audio, video, data, etc.) to a remote medical professional for review. In some implementations, the head-mounted device 101 is configured to be worn on a user's head, and the command unit 121 is configured to be worn on the user's body, such as mounted on a belt worn around the user's waist, as shown in FIGS. 1A-1F. However, this disclosure contemplates that the command unit 121 can be worn on other parts of the user's body. Alternatively or additionally, this disclosure contemplates that the command unit 121 can be incorporated into and/or attached to the head-mounted device 101. Therefore, the disclosure should not be limited to implementations where the command unit 121 is worn around a user's waist as shown in FIGS. 1A-1F.

Figure 2A:
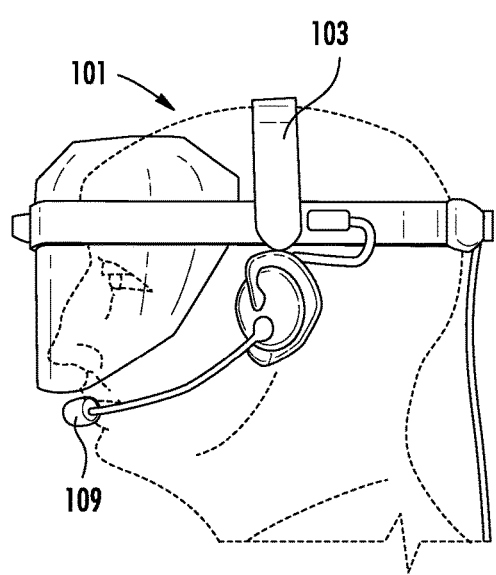
FIGS. 2A-2D are perspective views illustrating a head-mounted device included in the mobile assessment system of FIGS. 1A-1F.
Figure 2B:
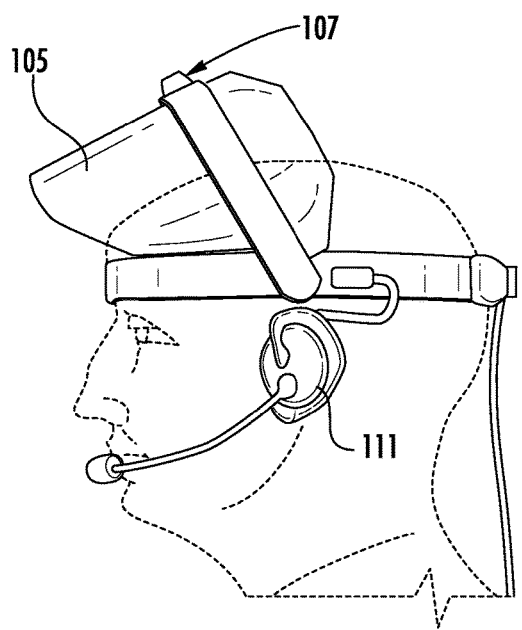
Figure 2C:
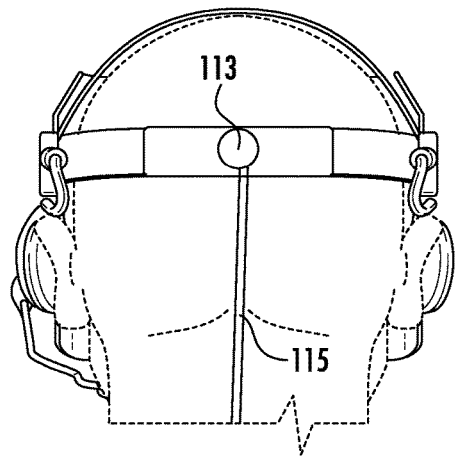

As shown in FIGS. 1B, 1C, 1E and 1F, the head-mounted device 101 and the command unit 121 can be communicatively connected by a communication link 115 (e.g., a first communication link). This disclosure contemplates the communication link 115 is any suitable communication link. For example, a communication link can be implemented by any medium that facilitates data exchange between the head-mounted device 101 and the command unit 121 including, but not limited to, wired, wireless and optical links. In particular, the head-mounted device 101 and the command unit 121 can optionally be connected by the communication link 115 through a command unit interface 113 and a head-mounted device interface 123, respectively. Additionally, the head-mounted device 101 can include a head-mounted frame 103 that is configured to hold a transparent visor 105. As used herein, a transparent visor is capable of transmitting light rays through the visor such that objects can be seen by the user through the transparent visor. Optionally, the transparent visor 105 can be capable of moving between an active position, which is shown in FIG. 2A, and an inactive position, which is shown in FIG. 2B. In some implementations, the transparent visor 105 is attachable directly or indirectly to the head-mounted frame 103 through a hinge device, for example. The transparent visor 105 can therefore be rotated between the active position and the inactive position. When in the active position, the transparent visor 105 shields at least a portion of the user's face.

The head-mounted device 101 can also include an image capturing device 107. The image capturing device 107 is attachable to at least one of the head-mounted frame 103 and the transparent visor 105. The image capturing device 107 can be configured to capture images of the local scene assessed by the user of the mobile assessment system. For example, the image capturing device 107 can be a forward-facing image capturing device capable of capturing images of the local scene as observed by the user of the mobile assessment system through the transparent visor 105. In some implementations, the image capturing device 107 is a video capturing device that is capable of capturing video images of the local scene as observed by the user of the mobile assessment system through the transparent visor 105. Alternatively or additionally, the image capturing device 107 is a light field camera (i.e., a plenoptic camera) that uses a microlens array to capture 4D light field information about the local scene. It should be understood that images captured by a light field camera can be virtually refocused at any time after image capture using a computing device. Accordingly, it is possible to analyze and extract information from the images (e.g., persons or objects present at the local scene) captured by the light field camera at a later time.

Figure 2D:
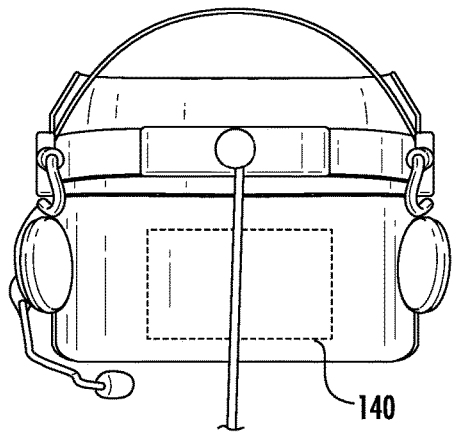

The head-mounted device 101 can also include a micro-optic display system. The micro-optic display system is attachable to at least one of the head-mounted frame 103 and the transparent visor 105. As shown in FIG. 2D, the micro-optic display system is configured to render a heads up image 140 on the transparent visor 105. For example, the micro-optic display system can include an image generator configured to generate and project the heads up image 140 on the transparent visor 105. Optionally, in some implementations, the head-mounted device 101 can also include a microphone 109 for detecting and recording the user's voice and/or at least one speaker 111 for projecting audio signals to the user. In some implementations, the at least one speaker 111 is configured to project audio signals exclusively to the user of the mobile assessment system (e.g., a speaker mode). For example, the at least one speaker 111 can be headphones or an earpiece. As such, the at least one speaker 111 facilitates communication between the user of the mobile assessment system and the remote station. Alternatively or additionally, the at least one speaker 111 can be configured to project audio signals to the user of the mobile assessment system, as well as one or more persons at the local scene (e.g., a conference mode). For example, the at least one speaker 111 can be a loudspeaker. In this case, the at least one speaker 111 can facilitate communication between anyone at the local scene and the remote station. The microphone 109 and the at least one speaker 111 are attachable to at least one of the head-mounted frame 103 and the transparent visor 105.

The mobile assessment system can also include an image capturing device control unit 131 configured to allow the user to control the image capturing device 107. As discussed above, the mobile assessment system is configured to facilitate the user having his hands free during an assessment of the local scene. Therefore, the mobile assessment system can be preconfigured for specific applications. However, the user may need to control some of the functions of the image capturing device 107, for example. The user may need to control functions including, but not limited to, pan, tilt and zoom (or magnification) functions of the image capturing device 107. It should be understood that the user can control pan and tilt functions by moving his head. In some implementations, the user receives instructions from the remote station (e.g., look left/right, look up/down, etc.). As discussed below, the user is aware of the image captured by the image capturing device 107 and transmitted to the remote station due to the heads up image 140 that is projected on the transparent visor 105, which facilitates the user determining where to look. Alternatively or additionally, the pan and tilt functions can be controlled mechanically (e.g., driven by motors, for example). It should be understood that mechanical control allows the remote station to control the pan and tilt functions independently of the user's head movement.

Additionally, the user may need to control the zoom function of the image capturing device 107. In some implementations, the user can manually control the zoom function of the image capturing device 107 using the image capturing device control unit 131 shown in FIG. 5. The image capturing device control unit 131 can be configured to facilitate simple operations. For example, in some cases, the user may be wearing protective gloves and may have difficulty making fine adjustments. Thus, the image capturing device control unit 131 can include switches, knobs, dials, buttons, etc. that are easy to operate. As shown in FIG. 5, the image capturing device control unit 131 includes a dial 135 and switches 137. The dial 135 is capable of rotating in the clockwise and counterclockwise directions, as well as acting as a switch, as shown by the arrows in FIG. 5. In addition, the switches 137 can have at least two positions. Thus, the image capturing device control unit 131 can be configured to control various image capturing device 107 functions, such as the zoom function, through manipulation of the dial 135 and/or the switches 137. For example, the amount of zoom may be adjusted by turning the dial 135 in the clockwise and counterclockwise directions. It should be understood that there are a number of possible configurations for the image capturing device control unit 131, and that the configuration of the image capturing device control unit 131 discussed above with regard to FIG. 5 is provided only as an example. This disclosure contemplates that the image capturing device control unit 131 can be configured to control optical zoom and/or digital zoom capabilities of the image capturing device 107.

In some implementations, the amount of zoom of the image capturing device 107 can be controlled using voice commands (e.g., zoom in, zoom out, stop zoom, etc.). For example, the voice commands can be issued by the user of the mobile assessment system or the remote station. When the voice commands are issued by the user, the voice commands can be received at the microphone 109 and transmitted from the head-mounted device 101 to the command unit 121 over the communication link 115. When the voice commands are issued by the remote station, the voice commands can be received by the command unit 121 over a communication link with the remote station, which is discussed in detail below. The command unit 121 can be configured to analyze the voice commands and correlate the voice commands with control signals. Thereafter, the command unit 121 can be configured to transmit the control signals to the head-mounted device 101 over the communication link 115. The amount of zoom of the image capturing device 107 can then be adjusted using the control signals, for example. Alternatively or additionally, the amount of zoom of the image capturing device 107 can be controlled using eye tracking technology, blink switching, etc. This disclosure contemplates that voice activation and/or eye tracking, blink switching, etc. can optionally replace or optionally augment manual control of the image capturing device 107.

Figure 3A:
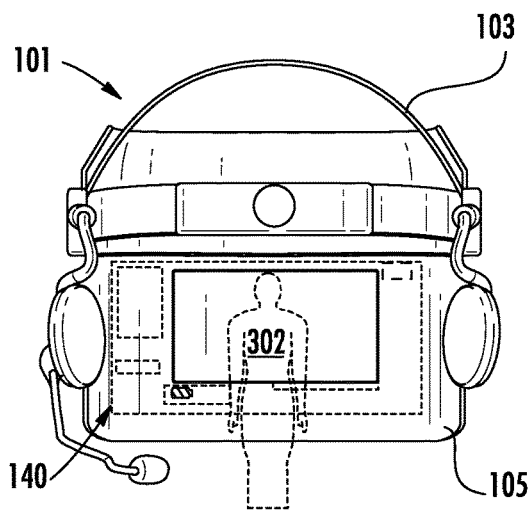
FIG. 3A is a perspective view illustrating a head-mounted device included in the mobile assessment system of FIGS. 1A-1F.
Figure 3B:
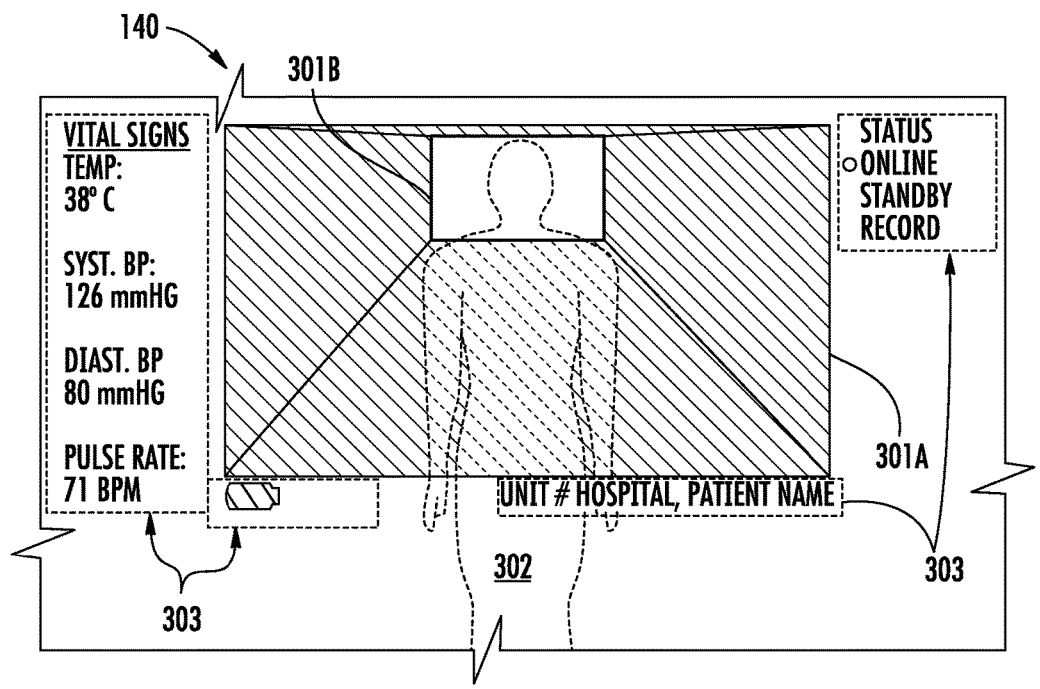
FIG. 3B illustrates an example local scene observed by a user of the head-mounted device of FIG. 3A.

Referring now to FIG. 3A, a perspective view illustrating a head-mounted device 101 included in the mobile assessment system of FIGS. 1A-1F is shown. As discussed above, the head-mounted device 101 can include a micro-optic display system configured to render the heads up image 140 on the transparent visor 105. As shown in FIG. 3A, in addition to the heads up image 140, the user can observe an object 302 (e.g., a person such as a patient, for example) at the local scene through the transparent visor 105. Referring now to FIG. 3B, an example scene observed by a user of the head-mounted device of FIG. 3A is shown. The heads up image 140 can include an outline of a field of view 301A, 301B of the image capturing device 107. The outline of the field of view 301A, 301B frames a scene that is captured by the image capturing device 107. Additionally, the outline of the field of view 301A, 301B defines boundaries of the image as observed at the remote station. The outline of the field of view 301A, 301B provides an indication to the user of the mobile assessment system of the image captured by the image capturing device 107 and transmitted to and viewed at the remote station.

The heads up image 140 can also include one or more graphical information fields 303. The graphical information fields 303 can include medical information such as a patient's identifying information (e.g., name, treatment center, etc.) and/or vital sign data, which can include, but is not limited to, temperature, blood pressure, heart rate, oxygen saturation and EKG data. In some implementations, the head-mounted device 101 or the command unit 121 can include or be communicatively connected to an interface configured to receive the vital sign data. For example, the interface can be a wireless receiver (e.g., a Bluetooth receiver, for example) configured to receive a patient's vital sign data from one or more medical instruments over a wireless communication link. The medical information can then be presented to the user as part of the heads up image 140 in the graphical information fields 303. Alternatively or additionally, the head-mounted device 101 can include a bar code reader system that is attachable to the head-mounted frame 103 or the transparent visor 105. The bar code reader system can facilitate obtaining information from the patient's medical record for presentation to the user as part of the heads up image 140 in the graphical information fields 303. Additionally, as discussed below, the patient identifying information and/or the vital sign data can be collected and transmitted to the remote station. Alternatively or additionally, the head-mounted device 101 or the command unit 121 can optionally include one or more sensors such as an infrared sensor or a radiation sensor, for example. This disclosure contemplates that information sensed/detected by the one or more sensors can be analyzed and then displayed as part of the heads up image 140 and/or communicated to the remote station. The information can be provided to both the user and the remote location.

The graphical information fields 303 can also include a status of the image capturing device 107. For example, the graphical information fields 303 can indicate whether the mobile assessment system is online, in standby or recording modes. When in the online mode, the head-mounted device 101 is in communication with the command unit 121. For example, the transparent visor 105 is in the active position (FIG. 2A) when the mobile assessment system is in the online mode. On the other hand, when in the standby mode, the head-mounted device 101 is not in communication with the command unit 121. For example, the transparent visor 105 is in the inactive position (FIG. 2B). When in the recording mode, the image capturing device 107 is activated and capturing images of the local scene. Alternatively or additionally, the graphical information fields 303 can indicate a level of battery charge. The graphical information fields 303 can also include extrinsic information. Extrinsic information is any type of information provided to the mobile assessment system from an external source such as the remote station, for example. The extrinsic information can optionally be information that is relevant and/or helpful to the user of the mobile assessment system. For example, the extrinsic information can include, but is not limited to, maps, diagrams, sketches, blueprints, weather data, situational data, identity data and expert/consultant recommendations or instructions. It should be understood that this disclosure contemplates that the extrinsic information is not limited to the above examples, and that the extrinsic information can include any type of information that can be displayed to a user of the mobile assessment system.

As shown in FIG. 3B, the heads up image 140 can include a first region that is defined by the outline of the field of view 301A, 301B and a second region that includes the graphical information fields 303. Optionally, the second region is located adjacent to the first region. For example, the second region can be located adjacent to the outline of the field of view 301A, 301B. In some implementations, the second region can be non-overlapping the first region. In other words, the graphical information fields 303 can be arranged outside of the outline of the field of view 301A, 301B such that the graphical information fields 303 do not overlap the outline of the field of view.

As discussed above, the micro-optic display system is configured to render the heads up image 140 on the transparent visor 105. In some implementations, the micro-optic display system can include an image generator configured to project the heads up image 140 on the transparent visor 105, a processor and a memory communicatively connected to the processor. The processor and the memory of the micro-optic display system are discussed below with regard to FIG. 7. The micro-optic display system can therefore be configured to determine the field of view and to determine the dimensions (e.g., angular extent, angle of coverage, etc.) of the field of view 301A, 301B. It should be understood that there are a number of methods for determining the field of view (or angle of view) of an image capturing device (e.g., the image capturing device 107). For example, the field of view of the image capturing device 107 can be calculated using information related to the operating characteristics of the image capturing device 107. The field of view can be calculated based the effective focal length of the lens (or lenses) and the size of the sensor (e.g., CCD, film, etc.) of the image capturing device 107, for example. Additionally, digital zooming (e.g., cropping and enlarging of a portion of the captured image) emulates the effect of increasing the effective focal length of the image capturing device 107. Accordingly, by receiving the operating characteristics of the image capturing device 107 such as the effective focal length and size of the sensor, it is possible to determine the dimensions of an outline of the field of view 301A, 301B.

Figure 4B:
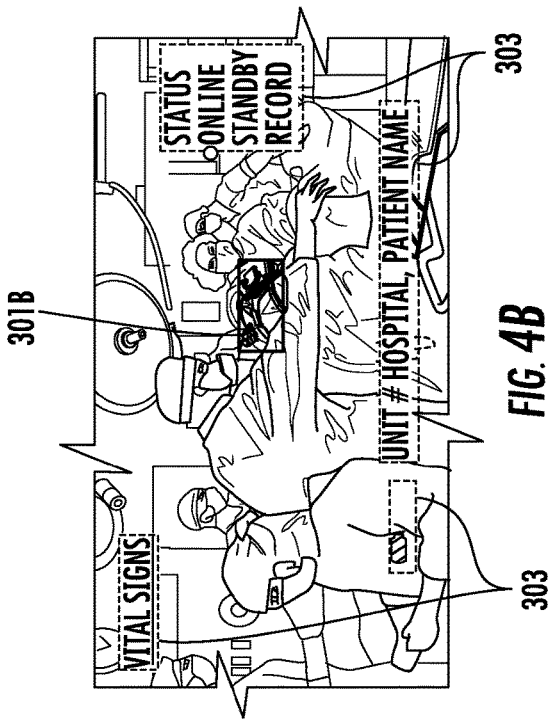
FIGS. 4A-4B illustrate example local scenes observed by a user of a head-mounted device included in the mobile assessment system of FIGS. 1A-1F.
Figure 4A:
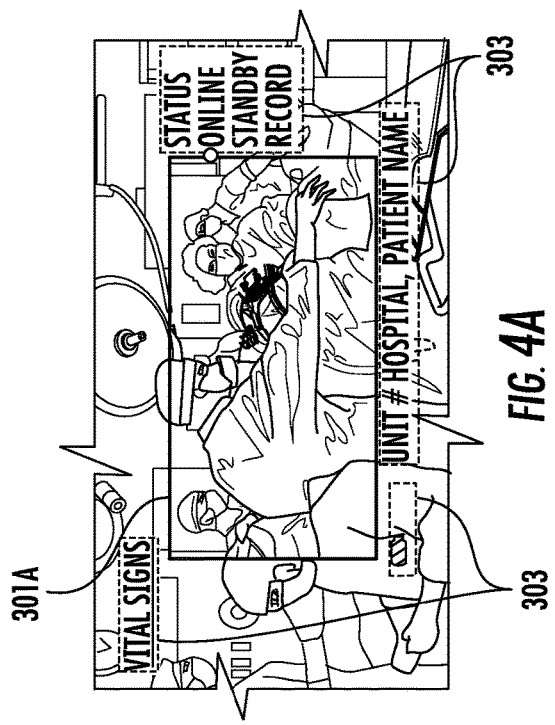
Figure 4D:
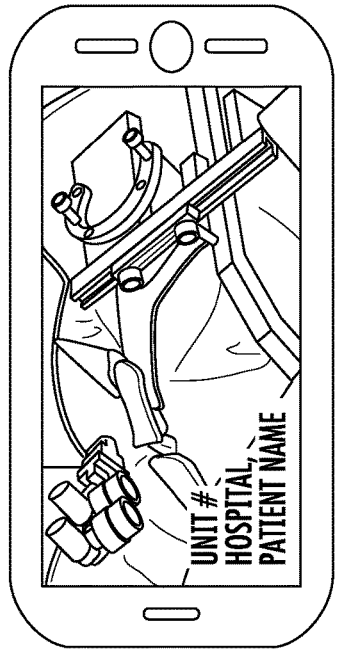
FIGS. 4C-4D illustrate example video images of the local scenes observed by the user in FIGS. 4A-4B as displayed on a remote display device.
Figure 4C:

In addition, the field of view (and the dimensions of the outline of the field of view 301A, 301B) change as the operating characteristics of the image capturing device 107 are varied. For example, when the amount of zoom (e.g., magnitude of magnification) is adjusted, the effective focal length of the image capturing device 107 changes. It should be understood that when the amount of zoom decreases, the effective focal length decreases, which corresponds to a widening of the field of view. This is shown in FIG. 3B as the outline of the field of view 301A. Additionally, FIG. 4A illustrates the outline of the field of view 301A for a wider field of view (e.g., a lesser magnitude of zoom) as seen by the user of the mobile assessment system on the transparent visor 105, while FIG. 4C illustrates the corresponding image as viewed at the remote station. On the other hand, when the amount of zoom increases, the effective focal length increases, which corresponds to a narrowing of the field of view. This is shown in FIG. 3B as the outline of the field of view 301B. Additionally, FIG. 4B illustrates the outline of the field of view 301B for a narrower field of view (e.g., a greater magnitude of zoom) as seen by the user of the mobile assessment system on the transparent visor 105, while FIG. 4D illustrates the corresponding image as viewed at the remote station. Therefore, as shown in FIGS. 4A-4D, the user of the mobile assessment system can observe the extent of the image as seen at the remote station because the outline of the field of view 301A, 301B of the image capturing device 107 is projected onto the transparent visor 105.

Figures 4E, 4F:
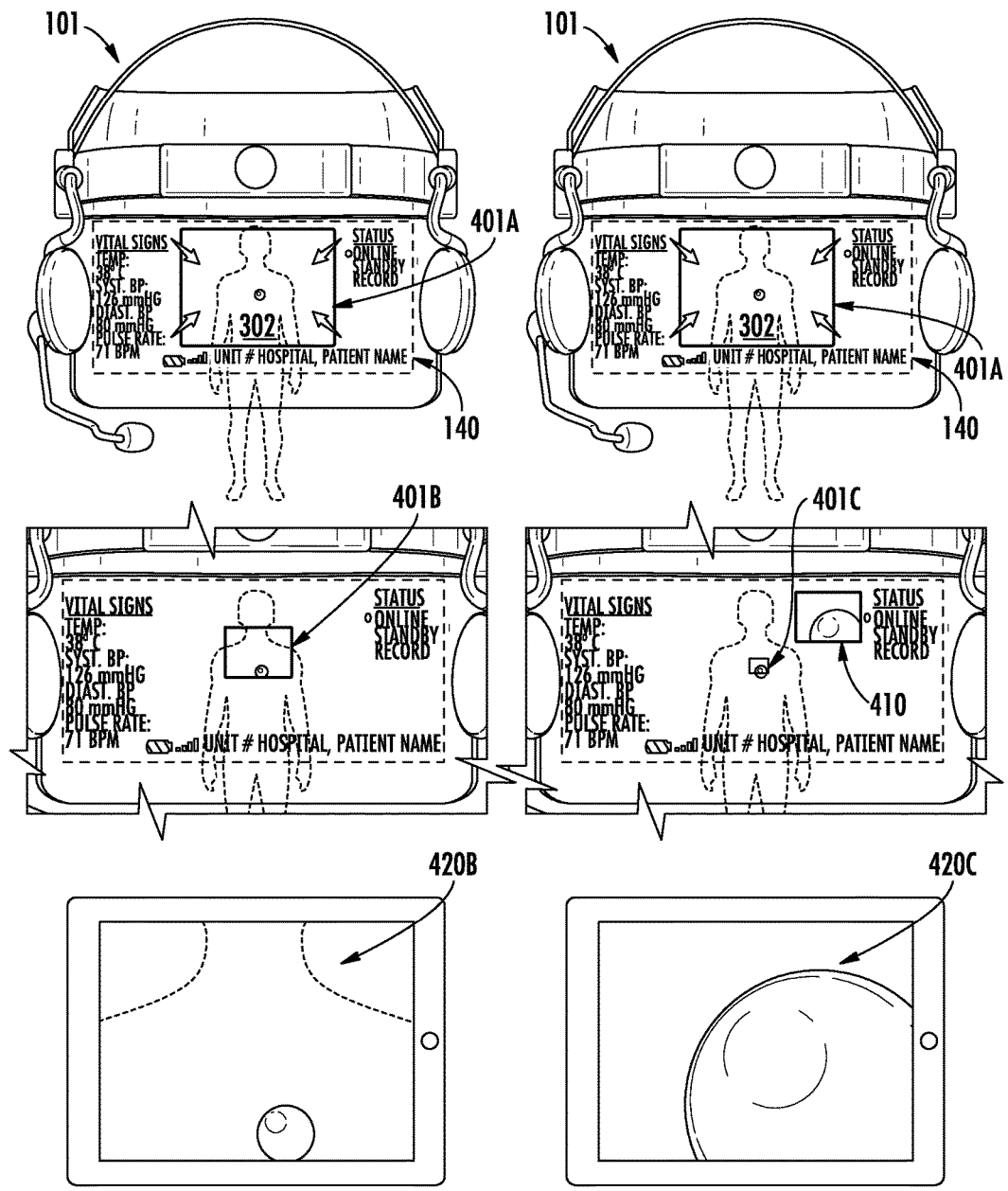
FIGS. 4E-4F illustrate an example local scene as observed by a user of a head-mounted device and corresponding video images of the local scene displayed at a remote station in a cone mode and a zoom mode, respectively.

Referring now to FIGS. 4E-4F, an example local scene as observed by a user of a head-mounted device and corresponding images of the local scene as displayed at a remote station in a cone mode and a zoom mode, respectively, are shown. Optionally, the head-mounted device 101 can be the head-mounted device of the mobile assessment system described with regard to FIGS. 1A-1F. Alternatively or additionally, the user of the head-mounted device 101 can optionally select the "cone mode" or the "zoom mode," for example, using the command unit (e.g., command unit 121), which is described in detail above. FIG. 4E illustrates the example local scene with an object 302 as observed by the user of the head-mounted device 101 and the corresponding image of the local scene as displayed at the remote station in the cone mode. As shown in FIG. 4E, while the user of the head-mounted device 101 operates the optical and/or digital zoom function of the image capturing device (e.g., image capturing device 107 described in detail above), the outline of the field of view shrinks in the heads up image 140 as shown by 401A (e.g., a wider field of view and/or lesser zoom) and 401B (e.g., a narrower field of view and/or greater zoom). For example, the outline of the field of view undergoes a reduction in size, and optionally a symmetrical reduction in size, while remaining in the user's line of sight. The head-mounted device 101 therefore provides the user with a hands-free, gaze forward heads up display with an unobstructed line of sight view of the local scene. The corresponding image 420B as displayed at the remote station for the narrower field of view and/or greater zoom is also shown in FIG. 4E. In other words the area of zoom or the area within the outline of the field of view 401B is displayed at the remote station.

FIG. 4F illustrates the example local scene with the object 302 as observed by the user of the head-mounted device 101 and the corresponding image of the local scene as displayed at the remote station in the zoom mode. Similar to FIG. 4E, as shown in FIG. 4F, while the user of the head-mounted device 101 operates the optical and/or digital zoom function of the image capturing device, the outline of the field of view shrinks in the heads up image 140 as shown by 401A (e.g., a wider field of view and/or lesser zoom) and 401C (e.g., a narrower field of view and/or greater zoom). For example, the outline of the field of view undergoes a reduction in size, and optionally a symmetrical reduction in size, while remaining in the user's line of sight. Optionally, in addition to the outline of the field of view 401C, a zoom box 410 can also be provided on the heads up image. The zoom box 410 can display a magnified view of a portion of the local scene contained within the outline of the field of view 401C, for example. The zoom box 410 is not required to reduce in size symmetrically with the outline of the field of view. The zoom box 410 can optionally be displayed on the heads up image without obstructing the user's line of sight (e.g., away from the user's line of sight). Optionally, the zoom box can be displayed at a peripheral portion of the heads up image such as above, below, left or right of the outline of the field of view. For example, in FIG. 4F, the zoom box 410 is provided in an upper right portion of the heads up image and away from the user's line of sight, which minimizes undue distractions. It should be understood that the location of the zoom box 410 in FIG. 4F is only provided as an example and that other locations of the zoom box on the heads up image are possible. With a slight gaze, the user of the head-mounted device can view the zoom box 410 and its magnified view of the portion of the local scene contained within the outline of the field of view. The head-mounted device 101 therefore provides the user with a hands-free, gaze forward heads up display with an unobstructed line of sight view of the local scene. The corresponding image 420C as displayed at the remote station for the narrower field of view and/or greater zoom is also shown in FIG. 4F. In other words the area of zoom or the area within the outline of the field of view 401C is displayed at the remote station.

As discussed above, the head-mounted device 101 and the command unit 121 are communicatively connected through the communication link 115. The command unit 121 can also include a command unit processor and a command unit memory that is communicatively connected to the processor. The command unit processor and the command unit memory are discussed in detail below with regard to FIG. 7. Therefore, the command unit 121 can be configured to receive data from the head-mounted device 101 over the communication link 115. This disclosure contemplates that the data transmitted from the head-mounted device 101 to the command unit 121 can be any type of data such as video data, audio data or any other type of data. The command unit 121 can also be configured to transmit the data over a communication link (e.g., a second communication link) to the remote station. It should also be understood that the command unit 121 can be configured to receive data from the remote station over the communication link. This disclosure contemplates that the communication link between the command unit and the remote station is any suitable communication link. For example, a communication link can be implemented by any medium that facilitates data exchange between the command unit 121 and the remote station including, but not limited to, wired, wireless and optical links. In some implementations, the communication link between the command unit and the remote station can be a mobile telecommunication link, a satellite link, a radiofrequency channel, a computer network link or any other type of communication link.

Additionally, the command unit 121 can be configured to provide communication security when transmitting/receiving data over the communication link between the command unit 121 and the remote station. For example, the command unit 121 can be configured to establish a secure connection with the remote station prior to transmitting the data over the communication link. Alternatively or additionally, the command unit 121 can be configured to encrypt the data prior to transmitting the data over the communication link. It should be understood that there are a number of methods for providing communication security and that this disclosure should not be limited to establishing a secure connection and encrypting the transmitted data, which are only provided as examples.

The mobile assessment system can be used to provide the remote station with audio, video and any other data in near-real time. For example, the command unit 121 can be configured to receive the data at the head-mounted device interface 113 over the first communication link 115 and transmit the data from the command unit 121 over the communication link to the remote station in near real-time. In addition, the mobile assessment system can be used to provide the remote station with audio, video and any other data after a period of delay (e.g., store and forward capability). For example, the command unit 121 can be configured to receive the data at the head-mounted device interface 113 over the first communication link 115. Then, the command unit 121 can be configured to store the data in the command unit memory. At a later time, the command unit 121 can be configured to establish a connection with the remote station and transmit the data over the communication link to the remote station. This can be particularly useful when the communication link between the command unit 121 and the remote station is not available or when the available bandwidth of the communication link between the command unit 121 and the remote station is insufficient to support transmission of the data.

Optionally, the command unit 121 can be configured to perform various types of image processing on the images captured by the image capturing device 107. For example, image processing techniques can be applied to change the quality, size, format, presentation, etc. of the captured images. Image processing techniques are well known in the art and are therefore not discussed at length here. In addition, the command unit 121 can be configured to perform a voice recognition algorithm or a facial recognition algorithm on the data. The voice recognition algorithm or the facial recognition algorithm can identify information related to a person or persons present at the local scene. For example, when the data received at the head-mounted device interface 113 includes audio data, the command unit 121 can be configured to perform a voice recognition algorithm on the audio data and identify at least one person using the voice recognition algorithm. Then, the command unit 121 can be configured to transmit to the head-mounted device 101 over the communication link 115 information relating to an identity of the at least one person. The information related to the identity of the at least one person can then be projected onto the transparent visor 105 as information in the graphical information fields 303 of the heads up image 140, for example. When the data received at the head-mounted device interface 113 includes video data, the command unit 121 can be configured to perform a facial recognition algorithm on the video data and identify at least one person using the facial recognition algorithm. Then, the command unit 121 can be configured to transmit to the head-mounted device 101 over the communication link 115 information relating to an identity of the at least one person. The information related to the identity of the at least one person can then be projected onto the transparent visor 105 as information in the graphical information fields 303 of the heads up image 140, for example. Optionally, it should be understood that the voice recognition algorithm or the facial recognition algorithm can also be performed at the remote location. For example, the command unit 121 can be configured to transmit the audio or video data to the remote station over the communication link and receive information relating to an identity of the at least one person from the remote station over the communication link. The information relating to the identity of the at least one person can be obtained by performing a voice recognition algorithm or a facial recognition algorithm at the remote station.

Figure 6:
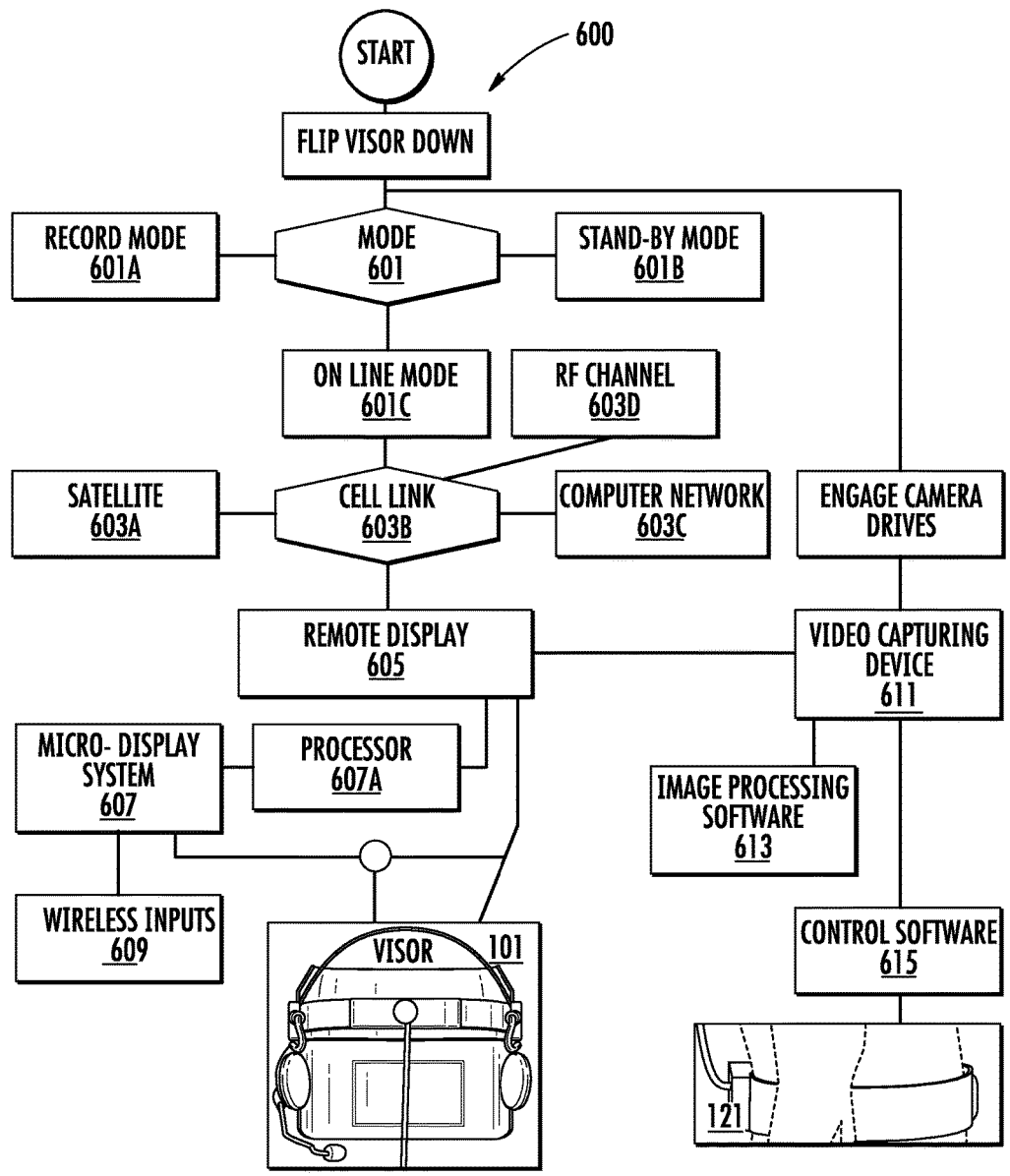
FIG. 6 is a block diagram illustrating a mobile assessment system according to implementations discussed herein.

Referring now to FIG. 6, a block diagram illustrating a mobile assessment system according to implementations discussed herein is shown. The mobile assessment system can include the head-mounted device 101 and the command unit 121, which are discussed in detail above. The mobile assessment system can operate in a plurality of modes 601 such as a record mode 601A (e.g., providing store and forward capability), a stand-by mode 601B (e.g., when the head-mounted device 101 and the command unit 121 are not communicatively connected) and an online mode 601C (e.g., when the head-mounted device 101 and the command unit 121 are communicatively connected). As discussed above, when the transparent visor 105 is in the active position (e.g., flipped down), the image capturing device such as the video capturing device 611 is in an operating state. The mobile assessment system is capable of transmitting data (e.g., audio, video, or any other data) to a remote station, which can be displayed on a remote display 605. This disclosure contemplates that the remote station can be a desktop computer, a laptop computer, a tablet computer, a mobile phone or other type of computing device having a remote display capability. The mobile assessment system can be communicatively connected to the remote station via a communication link including, but not limited to, a satellite link 603A, a cellular link 603B, a computer network 603C or a radiofrequency channel 603D. As discussed above, the head-mounted device 101 can include a micro-optic display system 607 configured to render a heads up image on a transparent visor. The heads up image can include an outline of the field of view of the video capturing device 611. Specifically, the micro-optic display system 607 can include a processor 607A that is configured to determine the dimensions of the outline of the field of view based on the operating characteristics of the video capturing device 611. Additionally, the mobile assessment system can include image processing software 613 for performing one or more image processes on the captured images, control software 615 for controlling functions of the video capturing device 611 and wireless inputs such as Bluetooth inputs 609 for receiving data from one or more external devices. It should be understood that the mobile assessment system discussed with regard to FIG. 6 is only one example system, and that the mobile assessment system can include more or less features as described with regard to FIG. 6.

It should be appreciated that the logical operations described herein with respect to the various figures may be implemented (1) as a sequence of computer implemented acts or program modules (i.e., software) running on a computing device, (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 7:
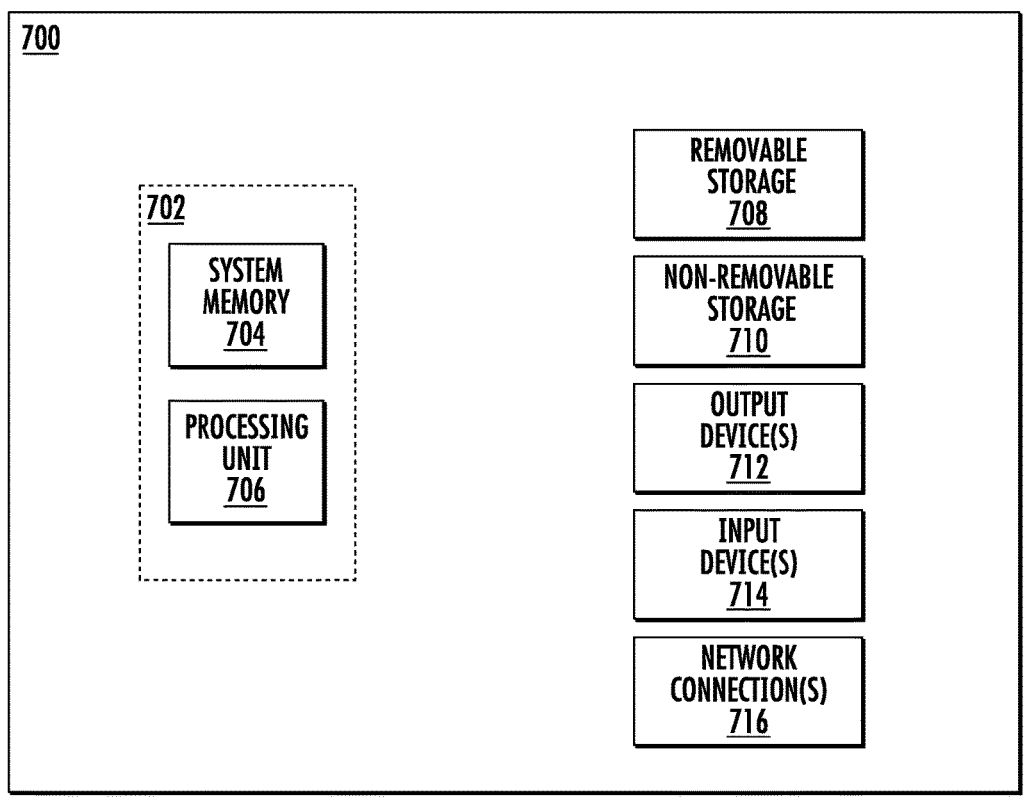
FIG. 7 is a block diagram of an example computing device.

When the logical operations described herein are implemented in software, the process may execute on any type of computing architecture or platform. For example, referring to FIG. 7, an example computing device upon which embodiments of the invention may be implemented is illustrated. In particular, the micro-optic display system and the command unit discussed above can include a computing device, such as computing device 700 shown in FIG. 7. The computing device 700 may include a bus or other communication mechanism for communicating information among various components of the computing device 700. In its most basic configuration, computing device 700 typically includes at least one processing unit 706 and system memory 704. Depending on the exact configuration and type of computing device, system memory 704 may be volatile (such as random access memory (RAM)), non-volatile (such as read-only memory (ROM), flash memory, etc.), or some combination of the two. This most basic configuration is illustrated in FIG. 7 by dashed line 702. The processing unit 706 may be a standard programmable processor that performs arithmetic and logic operations necessary for operation of the computing device 700.

Computing device 700 may have additional features/functionality. For example, computing device 700 may include additional storage such as removable storage 708 and non-removable storage 710 including, but not limited to, magnetic or optical disks or tapes. Computing device 700 may also contain network connection(s) 716 that allow the device to communicate with other devices. Computing device 700 may also have input device(s) 714 such as a keyboard, mouse, touch screen, etc. Output device(s) 712 such as a display, speakers, printer, etc. may also be included. The additional devices may be connected to the bus in order to facilitate communication of data among the components of the computing device 700. All these devices are well known in the art and need not be discussed at length here.

The processing unit 706 may be configured to execute program code encoded in tangible, computer-readable media. Computer-readable media refers to any media that is capable of providing data that causes the computing device 700 (i.e., a machine) to operate in a particular fashion. Various computer-readable media may be utilized to provide instructions to the processing unit 706 for execution. Common forms of computer-readable media include, for example, magnetic media, optical media, physical media, memory chips or cartridges, a carrier wave, or any other medium from which a computer can read. Example computer-readable media may include, but is not limited to, volatile media, non-volatile media and transmission media. Volatile and non-volatile media may be implemented in any method or technology for storage of information such as computer readable instructions, data structures, program modules or other data and common forms are discussed in detail below. Transmission media may include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 706 may execute program code stored in the system memory 704. For example, the bus may carry data to the system memory 704, from which the processing unit 706 receives and executes instructions. The data received by the system memory 704 may optionally be stored on the removable storage 708 or the non-removable storage 710 before or after execution by the processing unit 706.

Computing device 700 typically includes a variety of computer-readable media. Computer-readable media can be any available media that can be accessed by device 700 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 704, removable storage 708, and non-removable storage 710 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 700. Any such computer storage media may be part of computing device 700.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A head-mounted device, comprising:
    a head-mounted frame that is configured to hold a transparent visor;
    an image capturing device attachable to at least one of the head-mounted frame and the transparent visor;
    an interface configured to receive medical information, the interface having a wireless receiver configured to receive vital sign data for at least one patient from one or more medical instruments over a wireless communication link; and
    a micro-optic display system attachable to at least one of the head-mounted frame and the transparent visor, the micro-optic display system being configured to render a heads up image and the vital sign data on the transparent visor, wherein the heads up image comprises an outline of a field of view of the image capturing device and an outline of a field of view corresponding to an image as viewed at a remote work station, wherein the outline of the field of view corresponding to the image as viewed at the remote work station is dynamically displayed as a subset of the field of view of the image capturing device, the subset corresponding to a level of zoom on the image as viewed at the remote work station.

2. The head-mounted device of claim 1, wherein the outline of the field of view frames a scene captured by the image capturing device.

3. The head-mounted device of claim 1, further comprising an optical zoom control operable to control the level of zoom on the image as viewed at the remote work station, and resize the outline of the field of view corresponding to the image as viewed at the remote work station on the heads up image.

4. The head-mounted device of claim 1, wherein the micro-optic display system comprises:
    an image generator configured to project the heads up image on the transparent visor;
    a processor; and
    a memory communicatively connected to the processor having computer-executable instructions stored thereon that, when executed by the processor, cause the processor to: receive operating characteristics of the image capturing device; determine a field of view based on the operating characteristics; and determine dimensions of the outline of the field of view.

5. The head-mounted device of claim 4, wherein the operating characteristics of the image capturing device comprise at least one of an effective focal length and an amount of digital zoom.

6. The head-mounted device of claim 4 wherein the processor is operable to execute one or more instructions to receive the vital sign data for at least one patient from the one or more medical instruments and communicate the vital sign data to the micro-optic display system.

7. The head-mounted device of claim 6, wherein the wireless receiver comprises a Bluetooth receiver.

8. The head-mounted device of claim 1, wherein the heads up image further comprises a graphical information field.

9. The head-mounted device of claim 8, wherein the heads up image comprises a first region defined by the outline of the field of view and a second region including the graphical information field.

10. The head-mounted device of claim 1, further comprising at least one of a microphone attachable to at least one of the head-mounted frame and the transparent visor, or a speaker attachable to at least one of the head-mounted frame and the transparent visor.

11. The head-mounted device of claim 1, further comprising one or more sensors operably coupled to the head-mounted frame, the one or more sensors operable to capture infrared or radiation data.

12. A mobile assessment system comprising:
    a head-mounted frame that is configured to hold a transparent visor;
    a video capturing device attachable to at least one of the head-mounted frame and the transparent visor;
    an interface configured to receive medical information, the interface having a wireless receiver configured to receive vital sign data for at least one patient from one or more medical instruments over a wireless communication link;
    a micro-optic display system attachable to at least one of the head-mounted frame and the transparent visor, the micro-optic display system being configured to render a heads up image on the transparent visor,
        wherein the heads up image comprises an outline of a field of view of the image capturing device and an outline of a field of view corresponding to an image as viewed at a remote work station, wherein the outline of the field of view corresponding to the image as viewed at the remote work station is dynamically displayed as a subset of the field of view of the image capturing device, the subset corresponding to a level of zoom on the image as viewed at the remote work station; and, a remote work station communicatively engaged with the micro-optic display system, the remote work station having an interface operable to display a selected portion of the heads up image on the transparent visor.

13. The system of claim 12, wherein the outline of the field of view frames a scene captured by the video capturing device.

14. The system of claim 12, further comprising an optical zoom control operable to control the level of zoom on the image as viewed at the remote work station, and resize the outline of the field of view on the heads up image to correspond to the image as viewed at the remote work station.

15. The system of claim 12, wherein the micro-optic display system is operable to determine a field of view based on operating characteristics of the video capturing device; and determine dimensions of the outline of the field of view.

16. The system of claim 12, further comprising an interface configured to receive medical information corresponding to a subject in the outline of the field of view of the image capturing device.

17. The system of claim 16, wherein the medical information comprises vital sign data.

18. The system of claim 12, further comprising receiving, collecting, or detecting information at the local scene with the mobile assessment system, wherein the information comprises at least one of patient, medical, on-site, or extrinsic information.

19. The system of claim 18, further comprising transmitting the information to a remote expert over the communication link, and receiving one or more instructions from the remote expert over the communication link.

20. The system of claim 19, further comprising displaying the one or more instructions from the remote expert on the transparent visor using the micro-optic display system.

* * * * *